United States Patent
Skeete

(10) Patent No.: US 12,290,739 B2
(45) Date of Patent: May 6, 2025

(54) SYSTEM AND METHOD FOR TIMING PERSONAL PHYSICAL ACTIVITY

(71) Applicant: Oswald Leroy Skeete, Phoenix, AZ (US)

(72) Inventor: Oswald Leroy Skeete, Phoenix, AZ (US)

(*) Notice: Subject to any disclaimer, the term of this patent is extended or adjusted under 35 U.S.C. 154(b) by 883 days.

(21) Appl. No.: 17/410,905

(22) Filed: Aug. 24, 2021

(65) Prior Publication Data

US 2022/0054928 A1   Feb. 24, 2022

Related U.S. Application Data

(60) Provisional application No. 63/069,574, filed on Aug. 24, 2020.

(51) Int. Cl.
  *A63B 71/06*  (2006.01)
  *A63B 24/00*  (2006.01)

(52) U.S. Cl.
  CPC ...... *A63B 71/0686* (2013.01); *A63B 24/0062* (2013.01); *A63B 24/0075* (2013.01);
  (Continued)

(58) Field of Classification Search
  CPC .......... A63B 71/0686; A63B 24/0062; A63B 24/0075; A63B 71/0669; A63B 2220/12; A63B 2220/40; G07C 1/22
  See application file for complete search history.

(56) References Cited

U.S. PATENT DOCUMENTS

| 6,072,751 A | 6/2000 | Kirson |
| 2012/0274508 A1* | 11/2012 | Brown ............... A63B 24/0062 342/357.57 |

(Continued)

FOREIGN PATENT DOCUMENTS

| CN | 202777708 U | 3/2013 | |
| CN | 103561154 A * | 2/2014 | ............. G01C 21/12 |

(Continued)

OTHER PUBLICATIONS

Adidas Running App—Your Sports & Run Tracker, Google Play, https://play.google.com/store/apps/details?id=com.runtastic.android &hl=en.

(Continued)

*Primary Examiner* — Edwin A. Leon
*Assistant Examiner* — Kevin Andrew Johnston

(57) ABSTRACT

A system and method for timing personal physical activity provides an athlete with the ability to self-time runs over specific distances from anywhere. This can be used for any event that is timed over a specified distance. A software application utilizes the internal hardware commonly provided by many smart devices, such as global positioning system (GPS) modules and accelerometers, to assist the user in tracking and recording the time and distance of a walk/run. The software application is compatible with any smart devices, such as smart phones, smart watches, and a variety of other smart wearables. In addition, GPS is utilized to track and record the distance travelled by the user. The software application also uses a stopwatch-like mechanism in order to track and record the duration of an exercise. Furthermore, the GPS distance tracker and the stopwatch-like timer may be used together to create a pacemaker/pacesetter for the user.

7 Claims, 13 Drawing Sheets

(52) U.S. Cl.
CPC ...... *A63B 71/0669* (2013.01); *A63B 2220/12* (2013.01); *A63B 2220/40* (2013.01)

(56) References Cited

U.S. PATENT DOCUMENTS

| | | | |
|---|---|---|---|
| 2015/0116497 A1* | 4/2015 | Doval | G01S 7/412 |
| | | | 348/157 |
| 2016/0243426 A1* | 8/2016 | Griffin | A63B 69/0075 |
| 2017/0065871 A1* | 3/2017 | Galli | A63B 24/0062 |
| 2020/0065056 A1* | 2/2020 | Bastide | G06F 3/167 |

FOREIGN PATENT DOCUMENTS

| | | | | |
|---|---|---|---|---|
| GB | 2392109 A | * | 2/2004 | A63F 9/24 |
| GB | 2435113 A | * | 8/2007 | G04F 1/005 |

OTHER PUBLICATIONS

Luff, Christine, Best Running Apps Track your distance, progress, and more, Verywellfit.com, https://www.verywellfit.com/best-running-apps-4165816, Jul. 2, 2021.

Running Distance Tracker, Google Play, https://play.google.com/store/apps/details?id=com.fitness22.running&hl=en_IN.

* cited by examiner

SYSTEM AND METHOD FOR TIMING PERSONAL PHYSICAL ACTIVITY

The current application claims a priority to the U.S. Provisional Patent application Ser. No. 63/069,574 filed on Aug. 24, 2020.

FIELD OF THE INVENTION

The present invention relates to automatically recording time taken to run, walk, or swim a specific distance set by the user. More specifically, the present invention is a method that allows the user to mimic an athletic event, such as a 100 m or 200 m dash, without utilizing a track, a defined start or finish line, a starter, or a time piece based on the starter's gun. The software application coupled with a smart device like a phone or watch is used to activate and record the time and distance.

BACKGROUND OF THE INVENTION

Traditionally, an athlete may go to a track to practice or run their event of interest. Tracks are generally laid out with specific markers that translate to specific distances, like 100 meters, 200 meters etc. An athlete may typically be timed over a certain distance by a coach using a stopwatch. In the case of a competition, there will often be a starter with a gun connected to a timing mechanism. Furthermore, when running or walking, an athlete can use a watch or smartphone to keep track of the time and distance it took to complete a walk/run. In training or other such cases, however, athletes may not have access to a track, or a coach. After weeks, the same person may want to track the time and distance in order to quantitatively measure progress from the previous walk/run. One may use a stopwatch to track or time the walk or run but may not necessarily be able to track the distance unless they were on a track.

The present invention addresses this issue by giving the athlete the ability to self-time over a specific distance anywhere they choose. This can be used for any event that is timed over a specified distance. An objective of the present invention is to provide a software application utilizing the internal hardware of many smart devices, such as global positioning system (GPS) modules and accelerometers, to assist the user in tracking and recording the time and distance of a walk/run. The present invention uses a software application that is compatible with any smart devices, such as smart phones, smart watches, and a variety of other smart wearables. In addition, the present invention utilizes GPS to track and record the distance travelled by the user. The software application also uses a stopwatch-like mechanism in order to track and record the time ran by the user. Furthermore, the present invention utilizes the GPS distance tracker and the stopwatch-like timer together in order to create a pacemaker/pacesetter for the user, also known as a rabbit. The concept of a rabbit is well known and used in athletic completions (track and field meet).

DETAILED DESCRIPTION OF THE INVENTION

All illustrations of the drawings are for the purpose of describing selected versions of the present invention and are not intended to limit the scope of the present invention.

Figure 1:
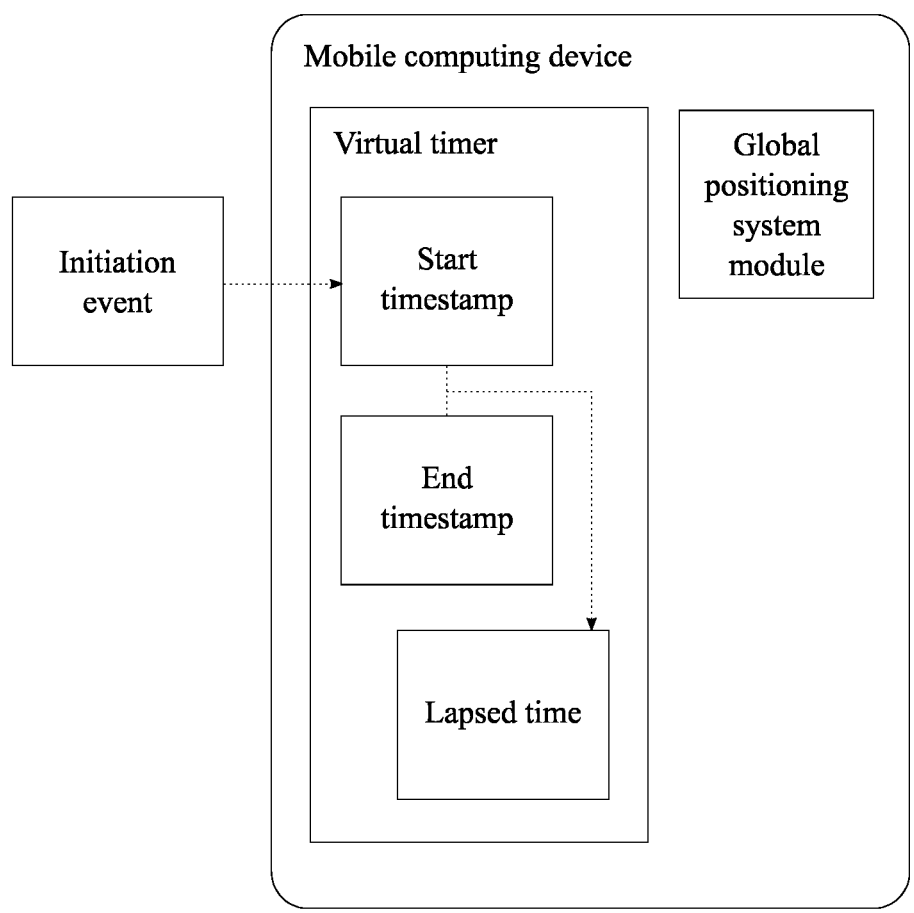
FIG. 1 is a block diagram illustrating the system of the present invention.

The present invention is a system and method for timing personal physical activity that allows an athlete to accurately time their physical activity without external assistance from a coach or other third party. The present invention accomplishes this by providing alternative mechanisms for determining the beginning and end of a workout or run. The system of the present invention includes a virtual timer managed by a mobile computing device, wherein the mobile computing device includes a global positioning system (GPS) module (Step A), as represented in FIG. 1. The virtual timer denotes an internal clock within the mobile computing device that allows for measurement of elapsed time. The mobile computing device may be any of standard phones, smart phones, smart wearables, laptops, personal computers, or other such devices capable of connecting wirelessly to the Internet and displaying relevant information to the user. The GPS module is the subsystem of the mobile computing device that enables tracking of the location of the mobile computing device.

Figure 2:
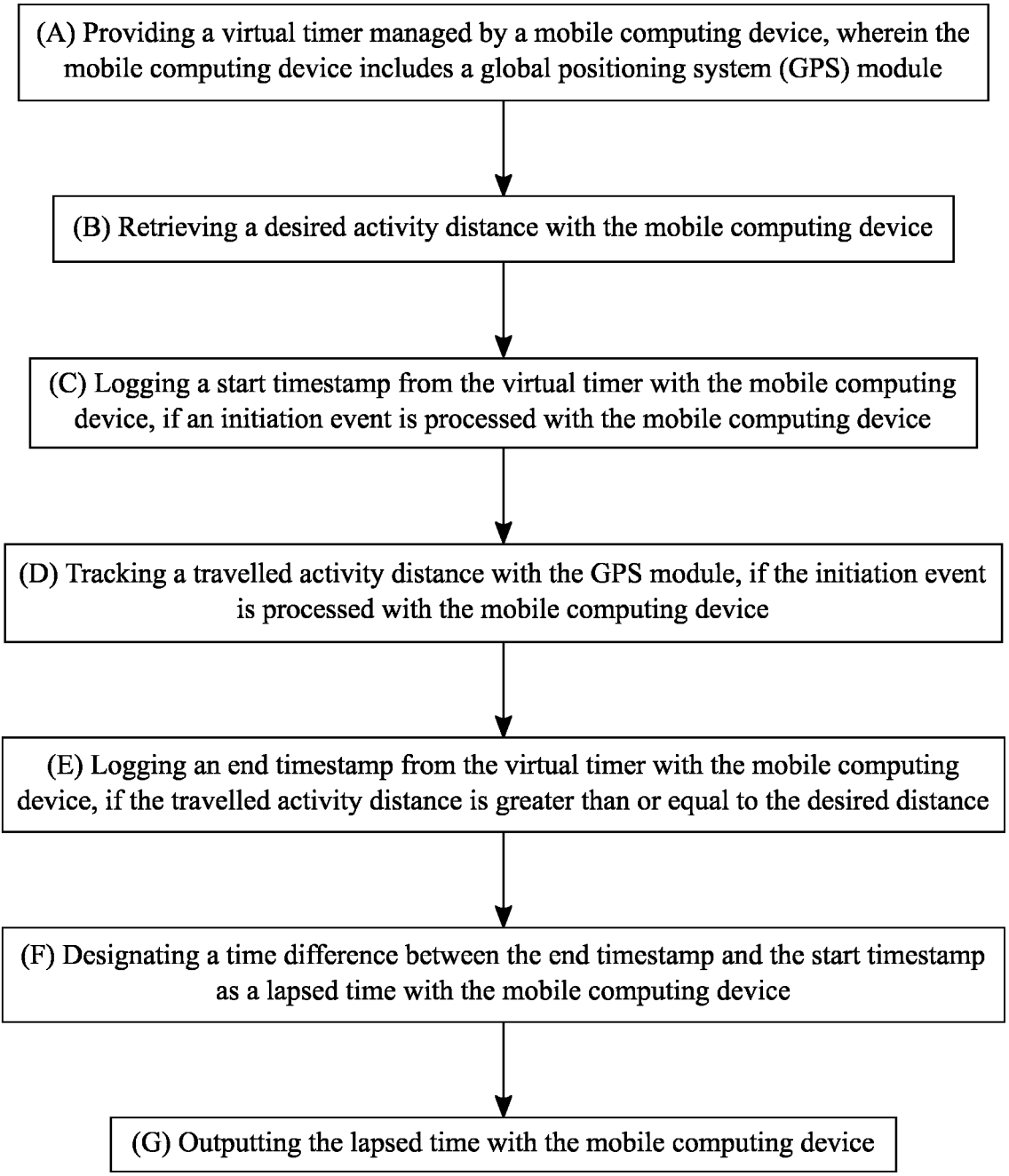
FIG. 2 is a flowchart illustrating the overall process for the method of the present invention.
Figure 3:
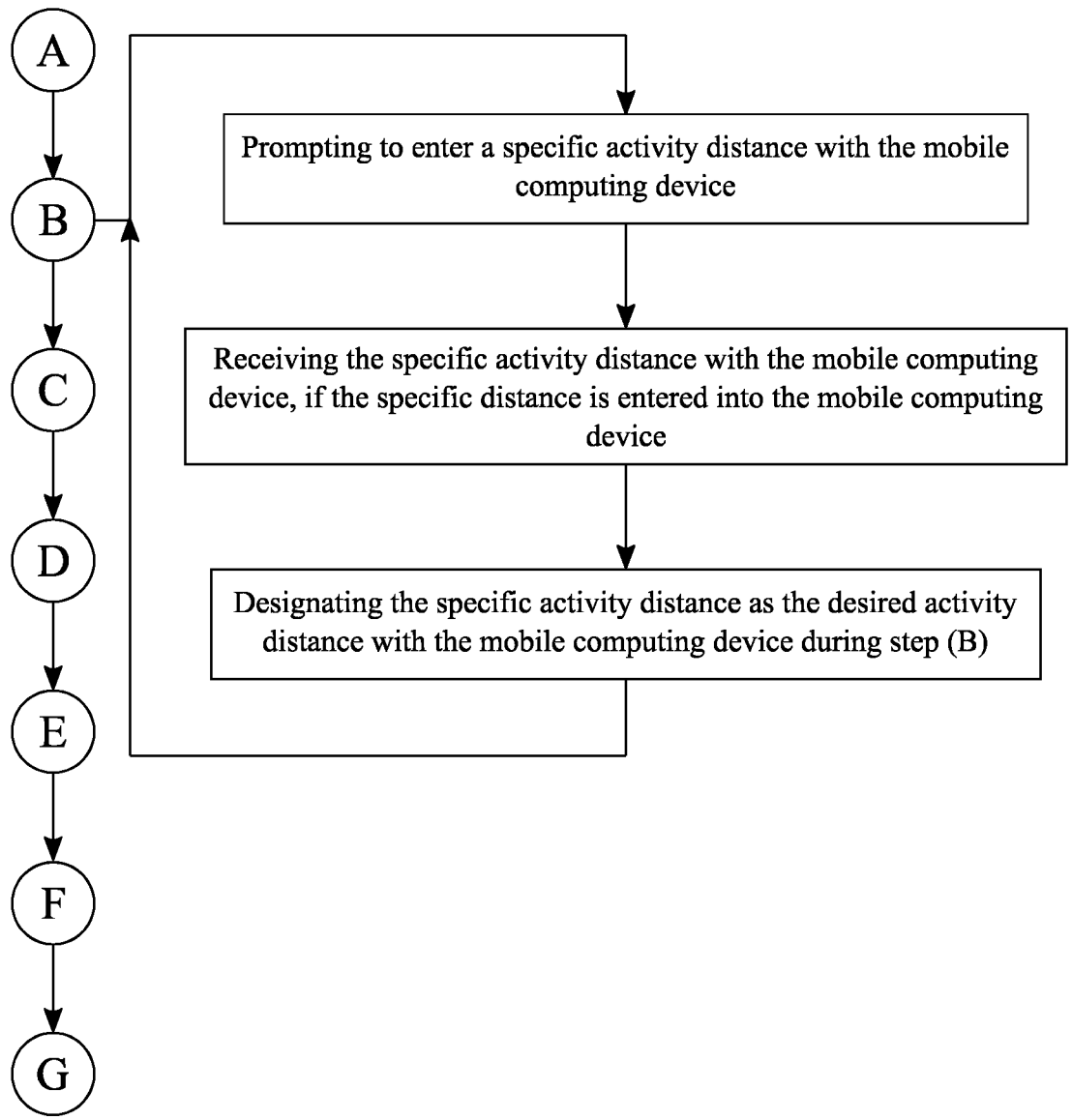
FIG. 3 is a flowchart illustrating a subprocess of accepting the desired activity distance.

The overall process followed by the method of the present invention allows for effective and efficient tracking, calculating, and reporting of the amount of time that passes as the user traverses a given distance. A desired activity distance is retrieved with the mobile computing device (Step B), as represented in FIG. 2. The desired activity distance denotes a recorded user input representing the distance the user wishes to traverse during exercise. Next, a start timestamp from the virtual timer is logged with the mobile computing device, if an initiation event is processed with the mobile computing device (Step C). The start timestamp is the moment representing the beginning of the workout, or, in some cases, the beginning of the meaningful, timed portion of the workout. The initiation event is an occurrence that indicates the beginning of the timed portion of a workout. Subsequently, a travelled activity distance is tracked with the GPS module, if the initiation event is processed with the mobile computing device (Step D). specific activity distance relates to a specified number of feet, meters, miles, or other units of measurement, but is not limited to any particular geographic arrangement; the specific activity distance may ultimately be traversed on flat, rough, or other terrain. The specific activity distance may then be received with the mobile computing device, if the specific distance is entered into the mobile computing device. This arrangement ensures that the mobile computing device has access to relevant data necessary to complete time elapsed computation. Finally, the specific activity distance may be designated as the desired activity distance with the mobile computing device during Step B. Thus, the mobile computing device may utilize user input in determining the appropriate outputs to calculate and subsequently display to the user.

Figure 4:
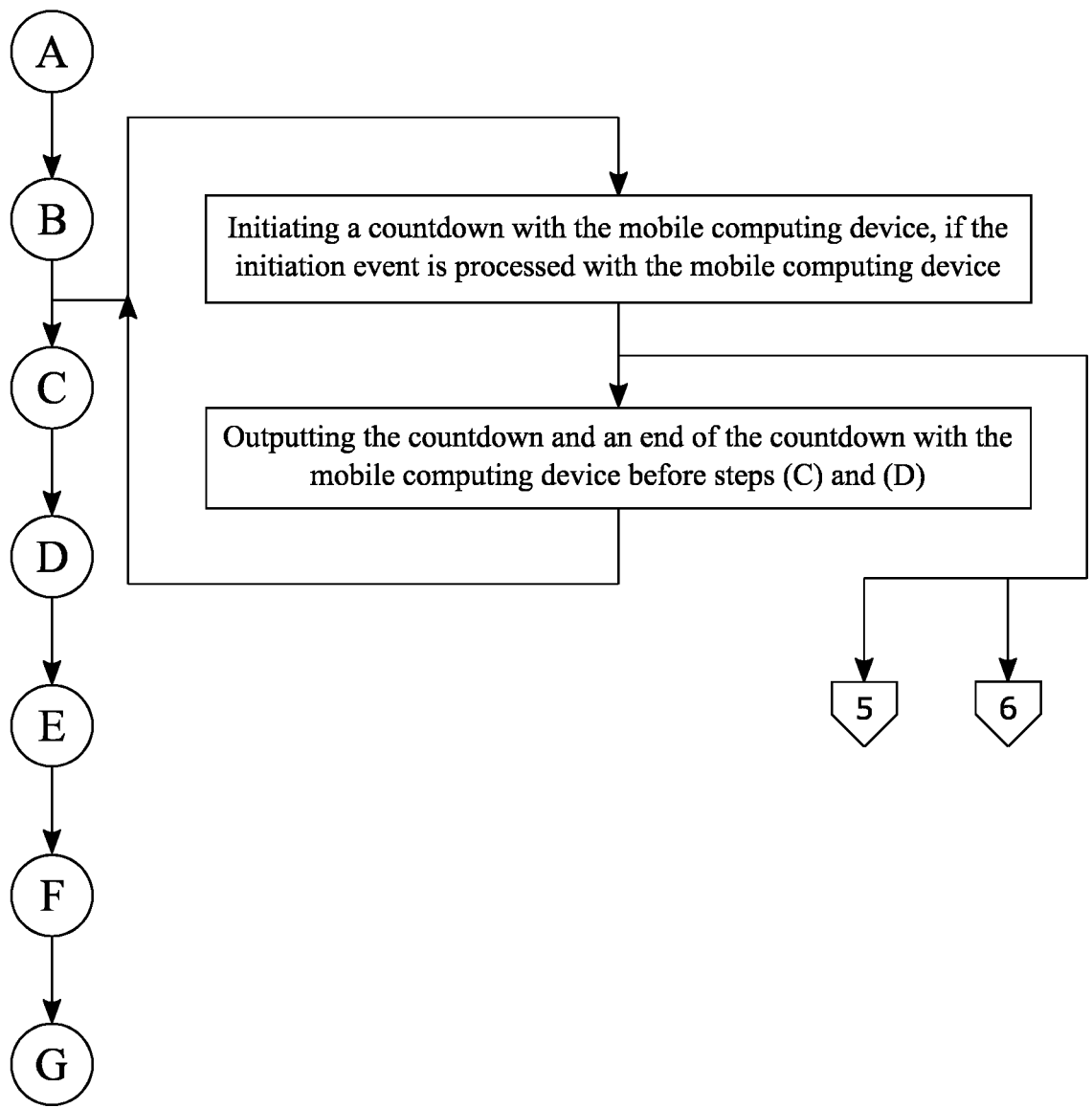
FIG. 4 is a flowchart illustrating a subprocess of beginning a countdown timer.

A user of the present invention may wish to start a workout upon completion of a countdown, thereby simulating race conditions. To achieve this, a countdown may be initiated with the mobile computing device, if the initiation event is processed with the mobile computing device, as represented in FIG. 4. The countdown is a periodic decrement of a numerical value to zero. The countdown and an end of the countdown may then be outputted with the mobile computing device before Steps C and D. Thus, a user may, in a preferred usage of the present invention, view the countdown before beginning exercise activity.

Figure 5:
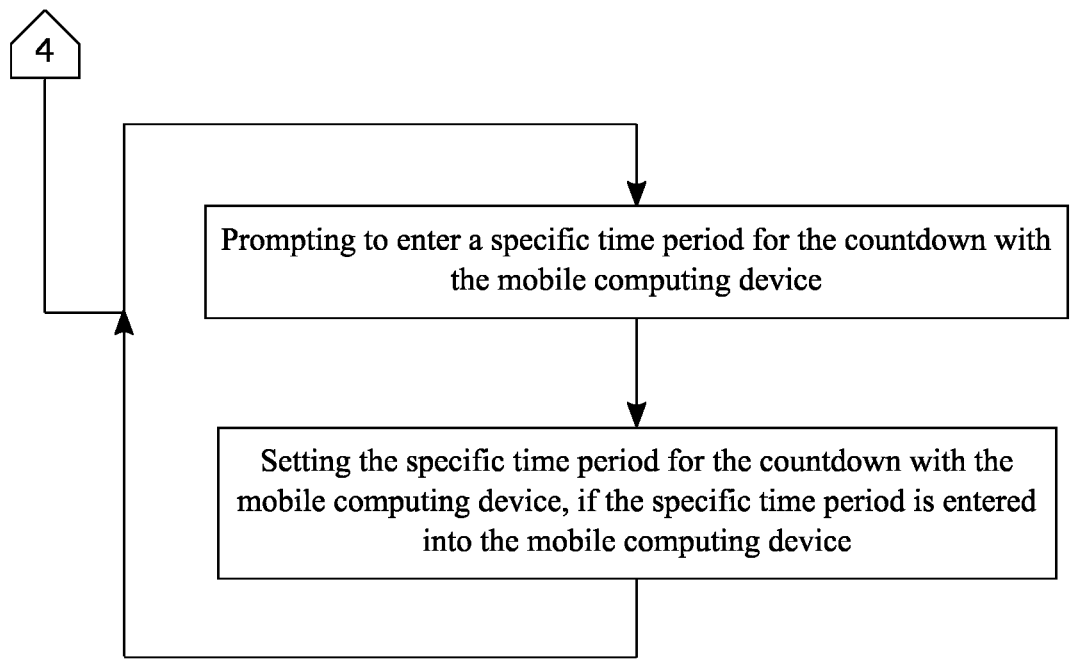
FIG. 5 is a flowchart illustrating a subprocess of specifying the countdown timer.

Furthermore, a user may benefit from specifying the length of a countdown in order to enable simulation of different race start conditions. To this end, a specific time period for the countdown may be prompted to be entered with the mobile computing device, as represented in FIG. 5. The specific time period may be listed in seconds, milliseconds, minutes, hours, or other units as desired by the user. The specific time period for the countdown may subsequently be set with the mobile computing device, if the specific time period is entered into the mobile computing device. Thus, the mobile computing device may begin the countdown at a desired starting time.

Figure 6:
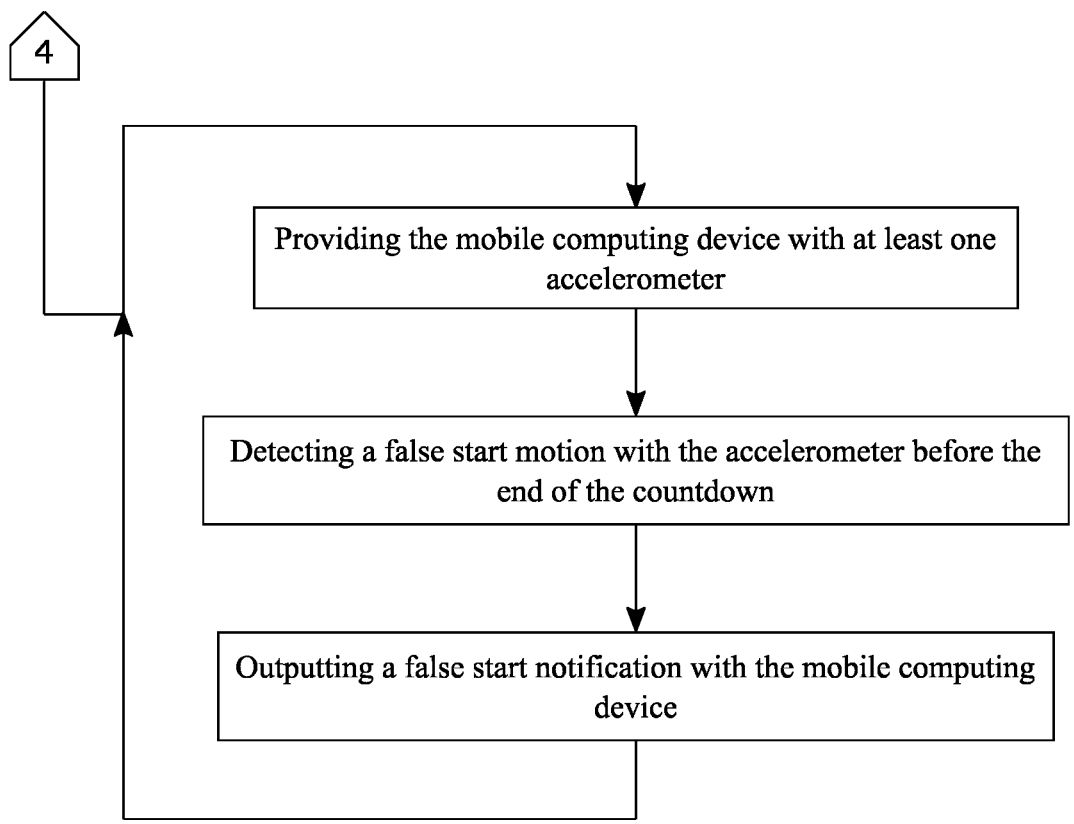
FIG. 6 is a flowchart illustrating a subprocess of detecting false starts.

An athlete may wish to practice or test their ability to respond to a starting gun, thereby simulating races. To achieve this, the mobile computing device may be provided with an accelerometer, as represented in FIG. 6. The accelerometer is a sensor capable of detecting changes in the position of the mobile computing device. A false start motion may be detected with the accelerometer before the end of the countdown. The false start motion may be any amount of movement registered by the accelerometer before the end of the countdown. Further, as it is common for racers to be required to wait until one-tenth of a second after the starting gun during many races, the detection of a false start motion may be delayed after the countdown as desired. Finally, a false start notification may be outputted with the mobile computing device. The false start notification may be any or any combination of visual, audio, or tactile alerts. Thus, the user may become aware of the false start and may subsequently practice reaction timing.

Figure 7:
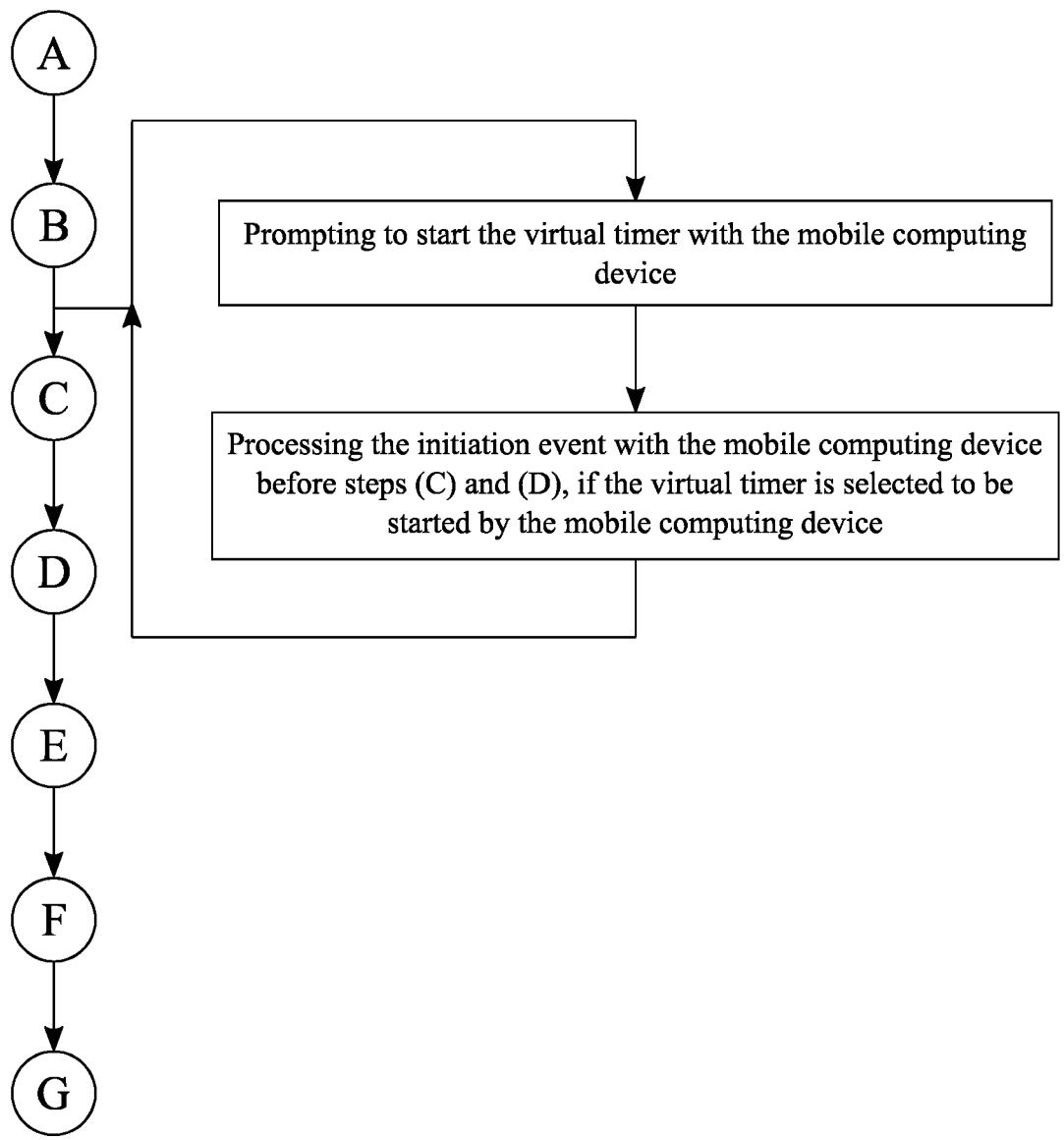
FIG. 7 is a flowchart illustrating a subprocess of beginning timing based on user input.

The user may wish to utilize the virtual timer as a regular timer. To enable this, the virtual timer may be prompted with the mobile computing device, as represented in FIG. 7. This enables the mobile computing device to collect and process user preferences prior to starting the virtual timer. Subsequently, the initiation event may be processed with the mobile computing device before Steps C and D, if the virtual timer is selected to be started by the mobile computing device. In this way, the virtual timer may be started according to the desire expressed by the user through accepting the prompt.

Figure 8:
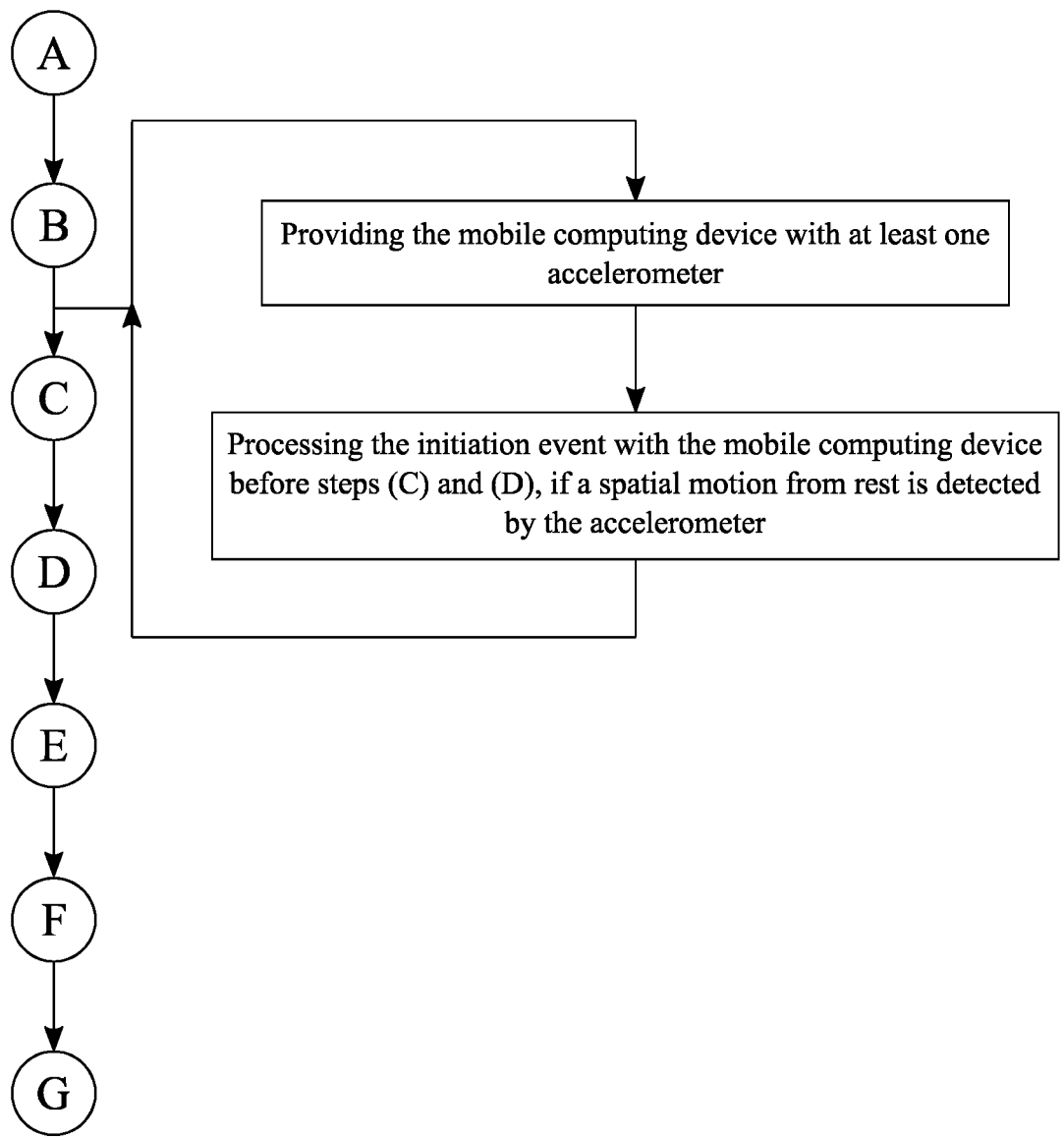
FIG. 8 is a flowchart illustrating a subprocess of beginning timing based on accelerometer input from an unmoving start.

The virtual timer is further equipped to begin timing an activity in response to the motion of the user. To enable this, the mobile computing device may be provided with at least one accelerometer, as represented in FIG. 8. The accelerometer is a sensor capable of detecting changes in the position of the mobile computing device. The initiation event may then be processed with the mobile computing device before Steps C and D, if a spatial motion from rest is detected by the accelerometer. The spatial motion from rest may be movement along any plane or vector. Thus, the virtual timer can begin tracking a workout or exercise activity as a user begins moving.

Figure 9:
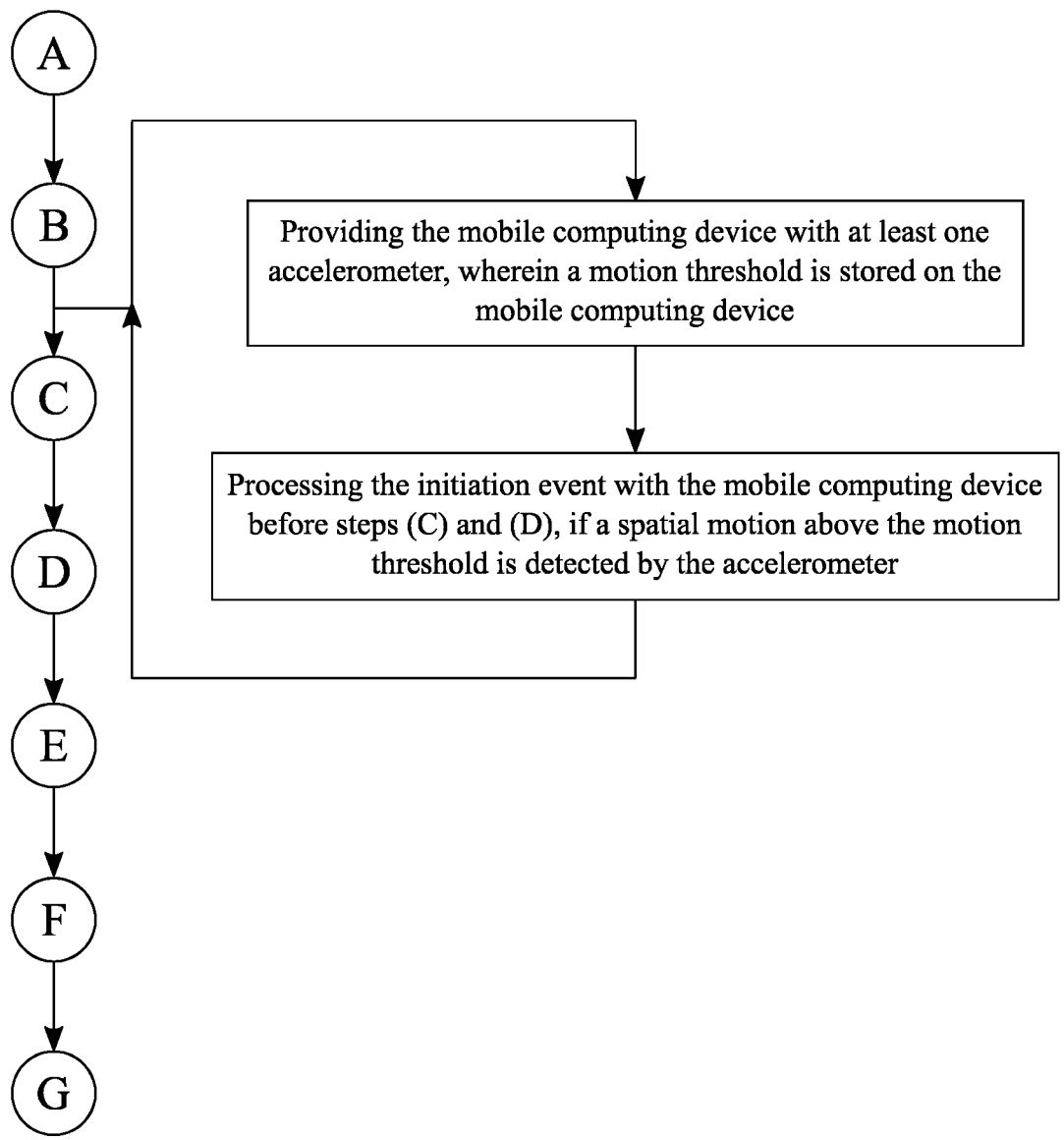
FIG. 9 is a flowchart illustrating a subprocess of beginning timing based on accelerometer input from a moving start.

It may be further desirable to prevent the mobile computing device from activating until an appropriate amount of movement is detected. To this end, the mobile computing device may be provided with at least one accelerometer, wherein a motion threshold is stored on the mobile computing device, as represented in FIG. 9. The motion threshold denotes a minimum value requirement that must be registered by the accelerometer before a signal can be sent. The initiation event may then be processed with the mobile computing device before Steps C and D, if a spatial motion above the motion threshold is detected by the accelerometer. This arrangement allows a user to get up to a desired speed and subsequently time the duration of high-speed movement during a workout.

Figure 10:
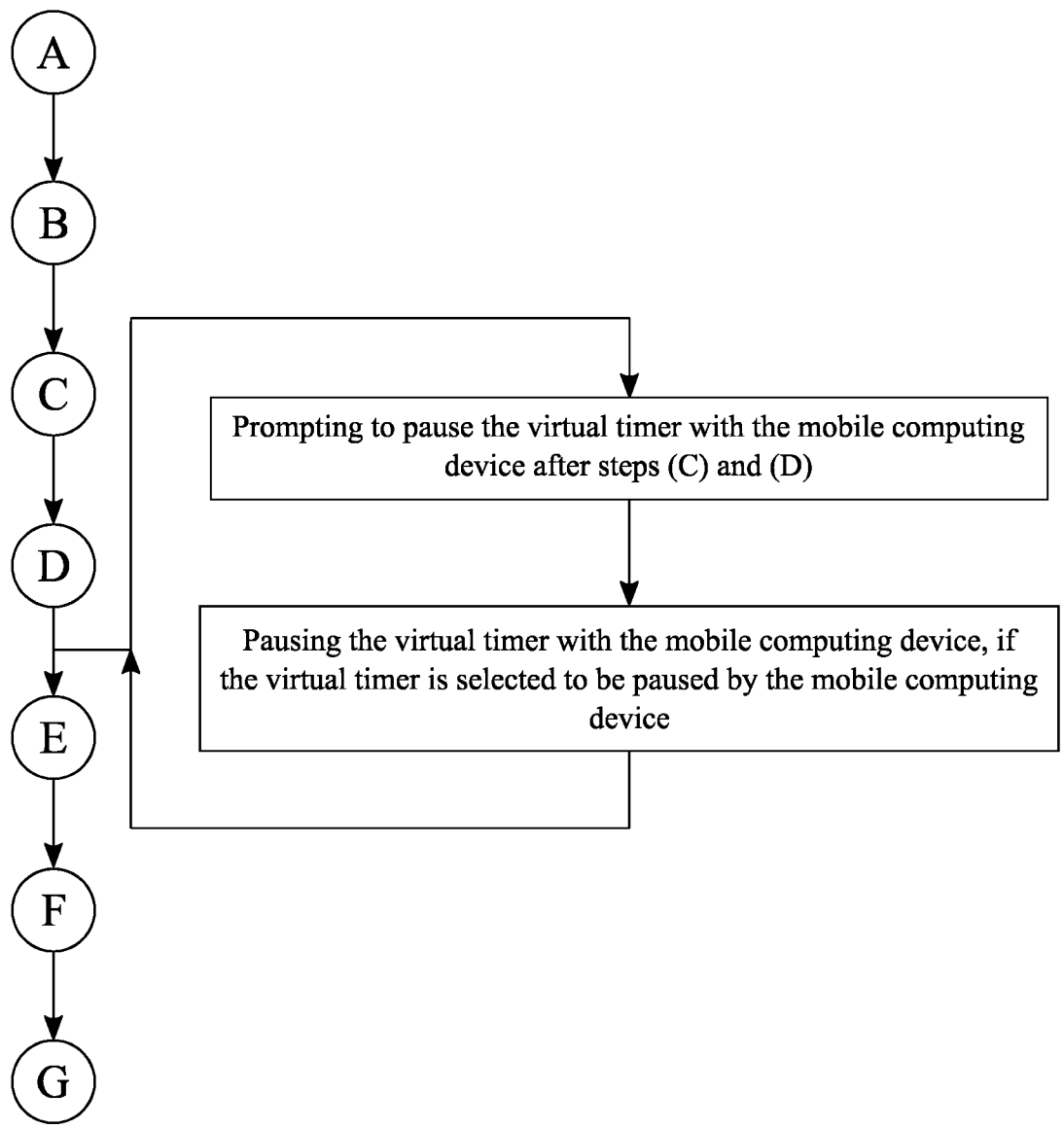
FIG. 10 is a flowchart illustrating a subprocess of pausing the timer.

A user may wish to pause a workout to take a break, or to enable different types of interval training. To allow for this, the user may be prompted to pause the virtual timer with the mobile computing device after Steps C and D, as represented in FIG. 10. This arrangement allows a user to decide whether to pause the timer during a workout or exercise session. The virtual timer may then be paused with the mobile computing device, if the virtual timer is selected to be paused by the mobile computing device. Thus, the user may prevent the virtual timer from counting during undesirable portions of a workout and may resume timing as desired.

Figure 11:
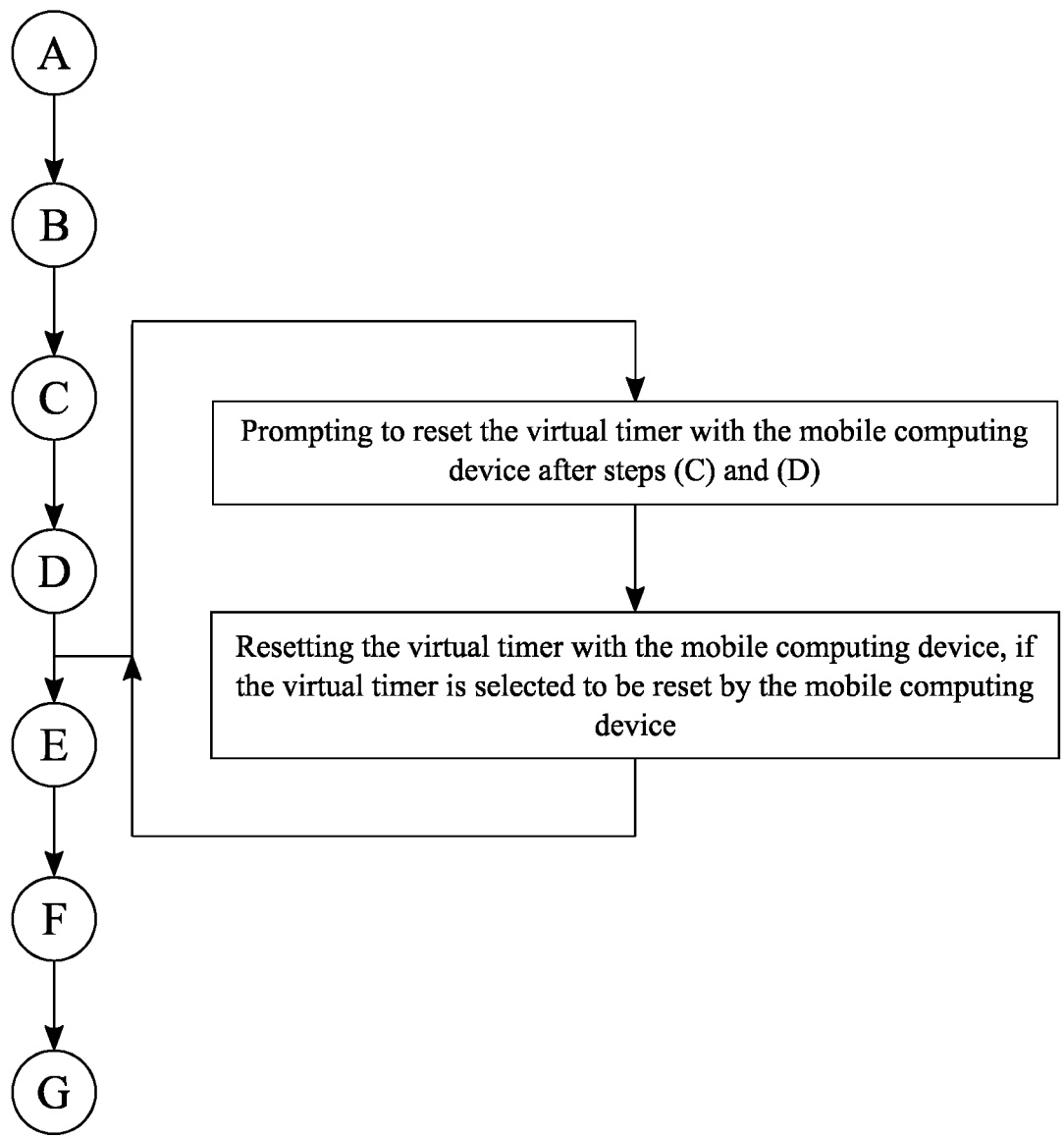
FIG. 11 is a flowchart illustrating a subprocess of resetting the timer.

It may further be desirable to allow a user to reset a workout, thus providing a fresh start point for a new workout. To this end, the user may be prompted to reset the virtual timer with the mobile computing device after Steps C and D, as represented in FIG. 11. This arrangement allows a user to decide whether to reset the timer upon completion of a workout or exercise session, or in order to break a workout into smaller segments. The virtual timer may then be reset with the mobile computing device, if the virtual timer is selected to be reset by the mobile computing device. In this way, the present invention may facilitate adjustments to a workout or exercise routine as desired.

Figure 12:
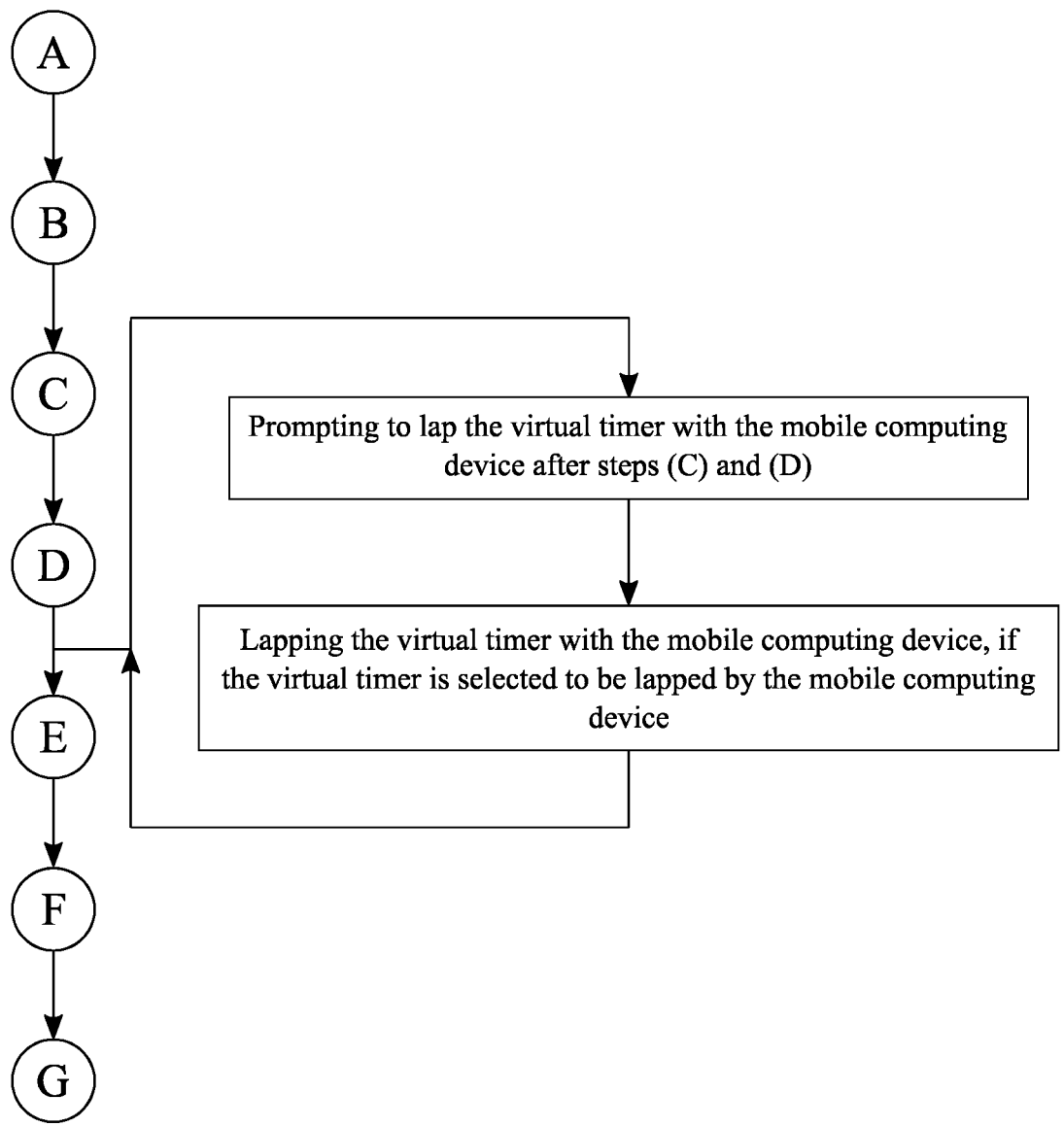
FIG. 12 is a flowchart illustrating a subprocess of lapping the timer.

Furthermore, a user may benefit from the ability to create multiple timestamps during a workout, thereby allowing the user to track progress at checkpoints. Therefore, the user may be prompted to lap the virtual timer with the mobile computing device after Steps C and D, as represented in FIG. 12. In this way, a user may decide to generate a time checkpoint in order to break a workout into smaller pieces or to track individual components of a multi-part workout. The virtual timer may then be lapped with the mobile computing device, if the virtual timer is selected to be lapped by the mobile computing device. This allows the present invention to break a larger workout into smaller pieces for subsequent review and analysis by the user.

Figure 13:
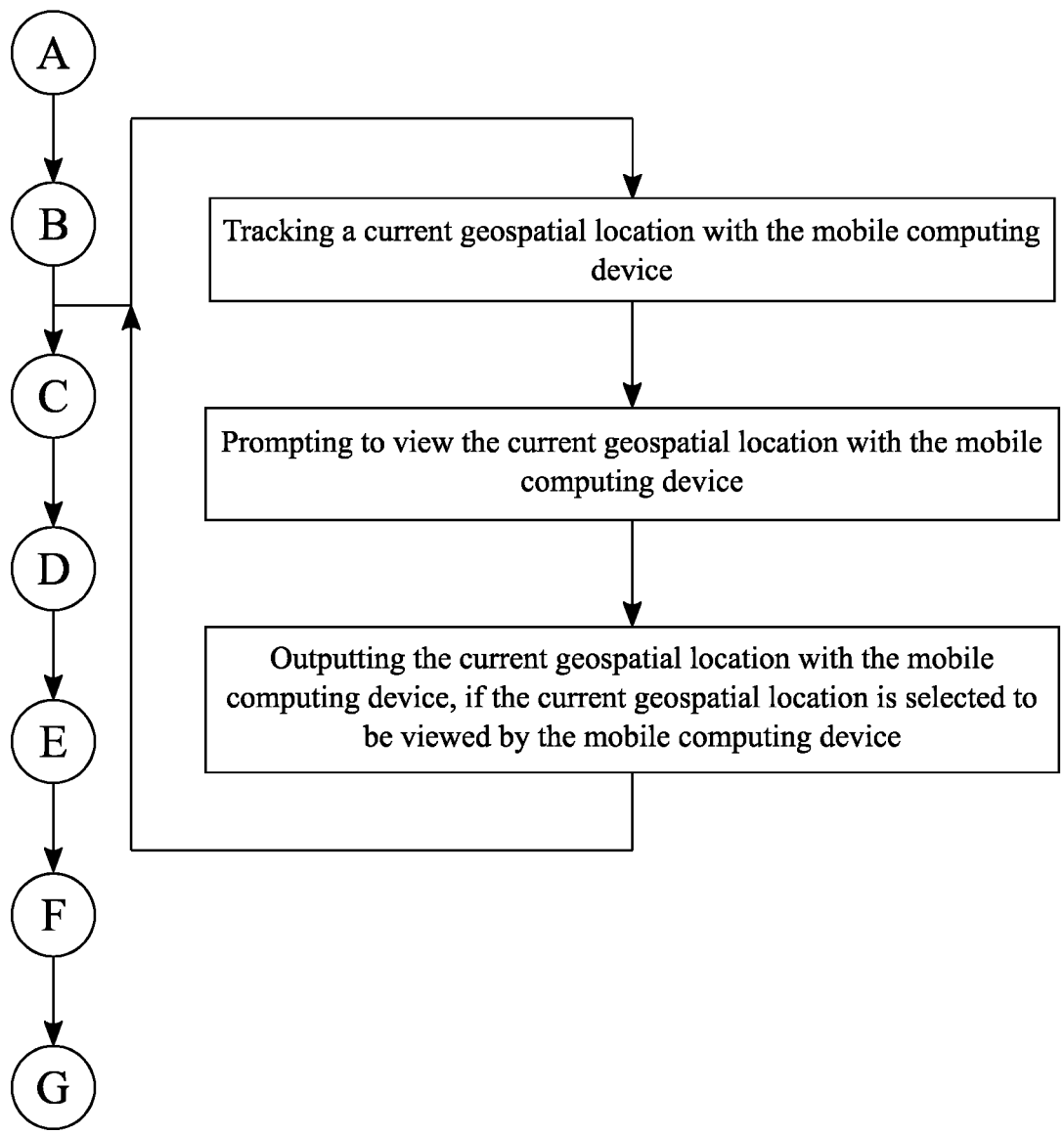
FIG. 13 is a flowchart illustrating a subprocess of utilizing location services.

A user may wish to view their location and progress during a workout. To allow for this, a current geospatial location may be tracked with the mobile computing device, as represented in FIG. 13. The GPS module may be used to collect geospatial coordinates for the mobile computing device during the workout. The user may next be prompted to view the current geospatial location with the mobile computing device. In this way, the user may determine whether to view a map or other visual indicator representing distance traveled during a workout. Finally, the current geospatial location may be outputted with the mobile computing device, if the current geospatial location is selected to be viewed by the mobile computing device. The current geospatial location may be presented in any of a variety of different informative formats capable of communicating all relevant information to the user.

Although the invention has been explained in relation to its preferred embodiment, it is to be understood that many other possible modifications and variations can be made without departing from the spirit and scope of the invention as hereinafter claimed.

What is claimed is:

1. A method of timing personal physical activity comprising the steps of:
   (A) providing a virtual timer managed by a mobile computing device, wherein the mobile computing device includes a global positioning system (GPS) module, and wherein a graphic user interface is hosted by the mobile computing device;
   (B) retrieving a desired activity distance with the mobile computing device;
   (C) logging a start timestamp from the virtual timer with the mobile computing device, if an initiation event is processed with the mobile computing device;
   (D) tracking a travelled activity distance with the GPS module, if the initiation event is processed with the mobile computing device;
   (E) logging an end timestamp from the virtual timer with the mobile computing device, if the travelled activity distance is greater than or equal to the desired distance;
   (F) designating a time difference between the end timestamp and the start timestamp as a lapsed time with the mobile computing device;
   (G) outputting the lapsed time with the mobile computing device;
   sequentially executing steps (B) through (G);
   providing the mobile computing device with at least one accelerometer;
   prompting to enter a specific time period for a countdown through the graphic user interface;
   setting the specific time period for the countdown with the mobile computing device, if the specific time period is entered through the graphic user interface;
   initiating the countdown with the mobile computing device, if the initiation event is processed with the mobile computing device;
   outputting the countdown and an end of the countdown with the mobile computing device before steps (C) and (D);
   outputting a false start notification with the mobile computing device, if a false start motion is detected with the accelerometer before the end of the countdown, wherein the false start notification is a combination of audio, visual, and tactile output by the mobile computing device;
   tracking a current geospatial location with the GPS module;
   prompting to view the current geospatial location through the graphic user interface; and
   outputting the current geospatial location with the mobile computing device, if the current geospatial location is selected to be viewed by the mobile computing device, wherein the current geospatial location is visually displayed on a virtual geospatial map through the graphic user interface.

2. The method as claimed in claim 1 comprising the steps of:
   prompting to enter a specific activity distance through the graphic user interface;
   receiving the specific activity distance through the graphic user interface, if the specific distance is entered into the mobile computing device; and
   designating the specific activity distance as the desired activity distance with the mobile computing device during step (B).

3. The method as claimed in claim 1 comprising the steps of:
   prompting to start the virtual timer through the graphic user interface; and
   processing the initiation event with the mobile computing device before steps (C) and (D), if the virtual timer is selected to be started by the mobile computing device.

4. The method as claimed in claim 1 comprising the step of:
   processing the initiation event with the mobile computing device before steps (C) and (D), if a spatial motion from rest is detected by the accelerometer.

5. The method as claimed in claim 1 comprising the steps of:
   providing a motion threshold stored on the mobile computing device; and
   processing the initiation event with the mobile computing device before steps (C) and (D), if a spatial motion above the motion threshold is detected by the accelerometer.

6. The method as claimed in claim 1 comprising the steps of:
   prompting to pause the virtual timer through the graphic user interface after steps (C) and (D); and
   pausing the virtual timer with the mobile computing device, if the virtual timer is selected to be paused through the graphic user interface.

7. The method as claimed in claim 1 comprising the steps of:
   prompting to reset the virtual timer through the graphic user interface after steps (C) and (D); and
   resetting the virtual timer with the mobile computing device, if the virtual timer is selected to be reset through the graphic user interface.

* * * * *